United States Patent
De Boer et al.

[19]

[11] Patent Number: 5,925,717
[45] Date of Patent: Jul. 20, 1999

[54] PROCESS FOR HYDROGENATION OF CONJUGATED DIENE POLYMERS AND CATALYST COMPOSITIONS SUITABLE FOR USE THEREIN

[75] Inventors: Eric Johannes Maria De Boer; Bart Hessen; Adriaan Albert Van Der Huizen; Wouter De Jong; Adrianus Johannes Van Der Linden; Bart Johan Ruisch; Lodewijk Schoon; Heleen Johanna Augusta De Smet; Frederik Hendrik Van Der Steen; Hubertus Cornelis Thomas Lucianes Van Strien; Alan Villena; Judith Johanna Berendina Walhof, all of CM Amsterdam, Netherlands

[73] Assignee: Shell Oil Company, Houston, Tex.

[21] Appl. No.: 08/816,538

[22] Filed: Mar. 13, 1997

[51] Int. Cl.$^6$ ........................................ G08F 8/04
[52] U.S. Cl. .................. 525/338; 525/332.8; 525/332.9; 525/339
[58] Field of Search ...................... 525/338, 339

[56] References Cited

U.S. PATENT DOCUMENTS

| | | | |
|---|---|---|---|
| 3,663,635 | 5/1972 | Lassau et al. | 260/666 P |
| 3,766,300 | 10/1973 | De La Mare | 260/879 |
| 3,898,208 | 8/1975 | Krause | 260/85.1 |
| 4,501,857 | 2/1985 | Kishimoto et al. | 525/338 |
| 5,541,272 | 7/1996 | Schmid et al. | 526/160 |

FOREIGN PATENT DOCUMENTS

| | | |
|---|---|---|
| 0434469 A2 | 12/1990 | European Pat. Off. |
| 0460725 B1 | 5/1991 | European Pat. Off. |
| 0471415 A1 | 8/1991 | European Pat. Off. |
| 0532099 A1 | 9/1992 | European Pat. Off. |
| 0544304 A1 | 11/1992 | European Pat. Off. |
| 0545844 A1 | 12/1992 | European Pat. Off. |
| 0549063 A2 | 12/1992 | European Pat. Off. |
| 0601953 A1 | 2/1994 | European Pat. Off. |
| 0 1289-805 | 11/1989 | Japan . |
| 2159819 | 4/1995 | United Kingdom . |
| 95/25136 | 3/1994 | WIPO . |

OTHER PUBLICATIONS

"Preparation and X–ray Structure of a Novel Chiral Methylene Bridged Titanocene Complex," by Christopher A. Willoughby, William N. Davis, Stephen L. Buchwald, *Journal of Organometallic Chemistry* 497, (1995) pp. 11–15.

"Mechanism of Acetylene Polymerization on the $NiCl_2$–$NaBH_4$ System in Alcohols," by N.S. Gorkova, F.S. Diachkovski, P.E. Matkovski, Chemical Abstracts, vol. 90, No. 4, Jan. 22, 1979, pp. 774–777.

*Primary Examiner*—Bernard Lipman
*Attorney, Agent, or Firm*—Donald F. Haas

[57] ABSTRACT

The invention provides a catalyst composition for hydrogenation of polymers containing ethylenical unsaturation which comprises at least:

(a) a titanium compound of the formula $$A_1\diagdown\hspace{-0.3em}\diagup L_1$$
$$\phantom{xxx}Ti$$
$$A_2\diagup\hspace{-0.3em}\diagdown L_2$$

(I) wherein $A_1$ represents an optionally substituted indenyl group of the formula

[structure showing indenyl with $(R_2)_n$ and $(R_1)_m$ substituents]

wherein substituents $R_1$ and $R_2$ may be the same or different and each may be selected from halogen, phenyl which optionally may bear one or more the same or different substituents, lower alkyl, alkoxy, phenoxy, phenylalkoxy, benzyl, and a bulky substituent containing one or more hetero atoms such as tri (loweralkyl)silyl, —$NPh_2$, —NHPh, —$BPh_2$, and —$B(OPh)_2$, wherein n may be an integer of from 0 to 4 and m may be an integer of from 0 to 3, (II) wherein $A_2$ has the same meaning as $A_1$ or alternatively represents an optionally substituted cyclopentadienyl group, and wherein $L_1$ and $L_2$ may be the same or different and each may be selected from hydrogen, halogen and preferred chlorine, lower alkyl, phenyl, aralkyl having from 7 to 10 carbons, a lower alkoxy group, phenyloxy, phenylalkoxy group having from 7 to 10 carbon atoms, carboxyl, carbonyl, a B-diketone coordination, a —$CH_2P$ $(Phenyl)_2$, —$CH_2$ Si(lower alkyl)$_3$ or —P(phenyl)$_2$ group; and (b) an alkali metal hydride, added as such or prepared in situ in the polymer solution from the alkali metal terminated living polymer and/or from additionally added alkali metal alkyl. The invention also concerns a process for hydrogenation of polymers containing ethylenical unsaturation using this catalyst.

15 Claims, No Drawings

PROCESS FOR HYDROGENATION OF CONJUGATED DIENE POLYMERS AND CATALYST COMPOSITIONS SUITABLE FOR USE THEREIN

FIELD OF THE INVENTION

The present invention relates to a process for the hydrogenation of conjugated diene polymers and catalyst compositions suitable for use therein. More in particular the invention relates to a process for the hydrogenation of polymers and copolymers of conjugated diene polymers, using a hydrogenation catalyst composition comprising at least a titanium compound and a alkali metal compound.

BACKGROUND OF THE INVENTION

Numerous catalyst are known for the hydrogenation of compounds containing unsaturated double bonds, catalysts which may be classified into two groups:

(1) Heterogeneous catalysts, generally consisting of a metal such as Ni, Pd, Pt, Ru, etc., optionally deposited on a support such as carbon, silica, alumina, calcium carbonate, etc.; and (2) homogeneous catalysts such as (a) Ziegler catalysts consisting of a combination of an organic salt of Ni, Co, Fe, Cr, etc. and a reducing agent such as for instance organoaluminum compounds, and (b) single component organometallic compounds of Ru, Rh, Ti, La, etc.

Heterogeneous catalysts are widely used in industry, but compared with homogeneous catalysts they are less active and hence, in order to carry out the desired hydrogenation with these heterogeneous catalysts, large quantities of catalyst are needed and the reaction must be carried out at relatively high pressures and temperatures. The homogeneous catalysts are generally more active. A small amount of catalyst is sufficient and the hydrogenation reaction can be carried out under milder pressure and temperature conditions.

Polymers of conjugated dienes such as 1,3-butadiene and isoprene and the copolymers of these dienes with vinylaromatic monomers, e.g. with styrene, are widely used in industry as elastomers. These polymers contain double bonds in their chain, which permit their vulcanization, but whose presence causes a low resistance to ageing and oxidation. Some block copolymers of conjugated dienes and vinylaromatic hydrocarbons are used without vulcanization as thermoplastic elastomers, as transparent impact-resistant resins, or as modifiers or compatibilizers of polystyrene and polyolefin resins. However, these copolymers have a low resistance to ageing and oxidation by atmospheric oxygen and by ozone, due to the presence of double bonds in their chain. Hence, the use of these copolymers in applications requiring exposure to the external environment is limited. The resistance to oxidation by oxygen and ozone, and, in general, the resistance to ageing, may be considerably improved by hydrogenating these polymers to obtain total or partial saturation of the double bonds. Numerous processes have been proposed for the hydrogenation of polymers which contain olefinic double bonds. Two types of processes are generally involved: those which use the aforementioned supported heterogeneous catalysts and those using homogeneous catalysts of the Ziegler type or organometallic compounds of rhodium and titanium.

In the processes using supported heterogeneous catalysts, the polymer to be hydrogenated is first dissolved in a suitable solvent and then contacted with hydrogen in the presence of the heterogeneous catalyst. The contact of the reactants with the catalyst is difficult due to the relatively high viscosity of the polymer solution, to steric hindrances of the polymer chain, and to the high adsorption of the polymer which, once hydrogenated, tends to remain on the surface of the catalyst interfering with the access to the active centres of the nonhydrogenated polymer. Hence, to achieve complete hydrogenation of the double bonds, large quantities of catalyst and severe reaction conditions are required. Usually this causes decomposition and gelification of the polymer. Furthermore, in the hydrogenation of copolymers of conjugated dienes with vinylaromatic hydrocarbons, the aromatic nuclei are also hydrogenated and it is difficult to effect a selective hydrogenation of the double bonds of the polydiene units. Likewise, the physical separation of the catalyst from the solution of hydrogenated polymer is extremely difficult and in some cases complete elimination is impossible due to the strong adsorption of the polymer on the heterogeneous catalyst.

In processes using Ziegler-type catalytic systems (as mentioned hereinbefore), the reaction takes place substantially in a homogeneous medium and the hydrogenation of the copolymers may be carried out under mild pressure and temperature conditions. Moreover, by adequately selecting the conditions of hydrogenation it is possible to selectively hydrogenate the double bonds of the poly(conjugated diene) blocks without hydrogenating the aromatic rings of the poly(vinylaromatic hydrocarbon) blocks.

Nevertheless, the elimination of the catalyst residues from the reaction product—which is absolutely necessary because these residues have an unfavourable effect on the stability of the hydrogenated polymers—is a complicated and costly step. Other processes using other homogeneous catalysts, e.g. the rhodium compounds described in U.S. Pat. No. 3,898,208 and in Japanese patent JP 01,289,805 have the disadvantage of the high cost of the rhodium catalysts.

It is known that hydrogenation catalysts in which one of the components is a derivative of cyclopentadienyltitanium (U.S. Pat. No. 4,501,857) are used—necessarily in the presence of organolithium compounds—for the hydrogenation of the olefinic double bonds of the polymers of conjugated dienes. European Patent application 0460725 describes the use of a similar catalyst system for the hydrogenation of polymers that had been synthesised by means of an organolithium compound and which have been terminated by the addition of hydrogen, the presence of the lithium hydride formed in the final reaction being necessary in this case to generate an active catalyst. The examples of both publications use the compound bis(cyclopentadienyl) titanium dichloride ($Cp_2TiCl_2$).

To obtain more economical hydrogenation processes, present-day industry feels the need of having homogeneous catalysts available which are more effective that those currently known, which are stable and active in concentrations that are sufficiently low so as to be able to avoid the costly step of elimination of catalyst residues from the hydrogenated polymer. Therefore, one object of the present invention is to provide an improved hydrogenation process which will accomplish these goals. It will be appreciated that another object of the present invention is formed by a catalyst composition to be used for said process. As a result of extensive research and experimentation there has been surprisingly found such a catalyst and process aimed at.

SUMMARY OF THE INVENTION

Accordingly, the present invention relates to a catalyst composition for hydrogenation of polymers containing ethylenical unsaturation, which comprises at least:

(a) a titanium compound of the formula

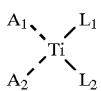

(I) wherein $A_1$ represents an optionally substituted indenyl group of the formula

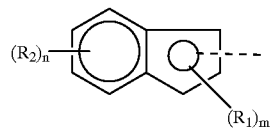

wherein the substituents $R_1$ and $R_2$ may be the same or different and each may be selected from halogen, phenyl which optionally may bear one or more of the same or different substituents, lower alkyl, lower alkoxy, phenoxy, phenylalkoxy, benzyl and a bulky substituent containing one or more hetero atoms such as tri (loweralkyl)silyl, —$NPh_2$, —NHPh, —$BPh_2$, and —$B(OPh)_2$, wherein n may be an integer of from 0 to 4, preferably from 0 to 2 and more preferably from 0 to 1, and m may be an integer of from 0 to 3, preferably from 0 to 2 and more preferably from 0 to 1, and (II) wherein $A_2$ has the same meaning as $A_1$ or alternatively represents an optionally substituted cyclopentadienyl group, and wherein $L_1$ and $L_2$ may be the same or different and each may be selected from hydrogen, halogen, preferably chlorine, lower alkyl, phenyl, aralkyl having from 7 to 10 carbons, a lower alkoxy group, phenyloxy, phenylalkoxy group having from 7 to 10 carbon atoms, carboxyl, carbonyl, a B-diketone coordination, a $CH_2P(phenyl)_2$, —$CH_2$ $Si(lower alkyl)_3$, or —$P(phenyl)_2$ group; and (b) an alkali metal hydride, added as such or prepared in situ in the polymer solution from the alkali metal terminated living polymer and/or from additionally added alkali metal alkyl.

The molar ratio of the alkali metal titanium is preferably at least 2:1. As alkali metal hydride is preferably used lithium hydride. The polymerisation initiator to be used for the starting living polymer of at least one conjugated diene and the optional additional amounts of alkali metal compound to form additional alkali metal hydride are preferably organolithium compounds. They are preferably selected from methyllithium, ethyllithium, n-propyl lithium, n-butyllithium, sec-butyl lithium, tert butyl lithium, n-hexyllithium, phenyl lithium, p-tolyl lithium, xyllithium, 1,4-dilithiobutane, alkylene dilithium, or a reaction product of butyl lithium and divinyl benzene.

Particularly preferred are n-butyl lithium, sec butyl lithium, tert-butyl lithium, and phenyllithium. Most preferred are tert butyllithium, sec-butyllithium, or n-butyllithium. The molar ratio of lithium hydride to titanium in the catalyst composition is preferably at least 6 and more preferably in the range of from 6 to 25.

The titanium compound (a) is normally used in amounts of from 5 to 100 mg per kg of conjugated diene polymer to be hydrogenated, and preferably in amounts from 20 to 60 mg/kg of conjugated diene polymer. Preferred ligands $L_1$ and $L_2$ in component (a) are selected from chlorine, bromine, carbonyl, methyl, ethyl, n-propyl, isopropyl, n-butyl, tert-butyl, sec-butyl, trimethylsilyloxy, benzyl, phenyl, hexyl, methoxy, ethoxy, n-propoxy, isopropoxy, butoxy, tert-butoxy, sec-butoxy, pentoxy, neopentoxy, phenoxy, phenylmethoxy, phenylethoxy, and a —$CH_2P$ $(phenyl)_2$ group. More preferably, $L_1$ and $L_2$ in the titanium catalyst component are both chlorine, benzyl, phenyl, methoxy, ethoxy, isopropoxy, tert-butoxy, n-butoxy, phenoxy, or a —$CH_2P(phenyl)_2$ group, and most preferably both are chlorine.

The cyclopentadienyl ring ($A_2$), if present, may optionally be substituted by one or more of the same or different groups, which may be selected from halogen or phenyl which optionally may bear one or more of the same or different substituents, lower alkyl, lower alkoxy, phenoxy, phenylalkoxy, benzyl, and a bulky substituent containing one or more hetero atoms such as tri (loweralkyl)silyl, —$NPh_2$, —NHPh, —$BPh_2$, and —$B(OPh)_2$. When one or more, and preferably one or two, of the symbols R represent phenyl, this may optionally be substituted by one or more substituents selected from lower alkyl, halogen, preferably fluoro or chloro, and lower alkoxy. Examples thereof are para-tert butylphenyl, pentafluorophenyl, dichlorophenyl, 3,5 di(t-butyl)-4-methoxy phenyl, and trifluorophenyl.

The most preferred titanium compounds are bis(1-indenyl) titanium dichloride, bis(1-indenyl) titanium diphenoxide, bis(1-indenyl) titanium dimethoxide, bis(1-methylindenyl) titanium dichloride, bis(5,6-dimethoxy-indenyl) titanium dichloride, bis(dimethoxyindenyl) titanium dichloride, bis(trimethyl-silylindenyl) titanium dichloride, (dimethoxyindenyl) (cyclopenta-dienyl) titanium dichloride, (dimethoxyindenyl) (indenyl) titanium dichloride, (dimethoxyindenyl) (indenyl) titanium dimethoxide, (methoxyindenyl) (indenyl) titanium dichloride, (methoxindenyl) (indenyl) titanium dimethoxide, (1-indenyl) (cyclopentadienyl) titanium dichloride, (1-indenyl) (cyclopentadienyl) titanium dimethoxide, and (1-indenyl) (cyclopentadienyl) titanium diphenoxide.

It will be appreciated that another aspect of the present invention is formed by a process for the hydrogenation of polymers containing ethylenical unsaturation (double C—C bonds) by bringing a polymer solution in intensive contact with hydrogen in the presence of at least the catalyst composition components (a) and (b).

According to a more preferred embodiment of the hydrogenation process of the present invention one or more promoters (c) may be present in addition to the beforementioned catalyst components (a) and (b). Said promoters (c) can be selected from polar ketone compounds, hydroxy group-containing ketone compounds, aldehyde compounds, ester compounds, lactone compounds, lactam compounds, epoxy compounds, and a reducing organometal compound. Of the beforementioned promoters especially preferred are ketone compounds, hydroxy group-containing ketone compounds, aldehyde compounds, ester compounds, and epoxy compounds.

Specific examples of preferred ketone compounds include acetone, diethyl ketone, di-n-propyl ketone, di-i-propyl ketone, di-sec-butyl ketone, di-t-butyl ketone, methyl ethyl ketone, i-propyl methyl ketone, i-butyl methyl ketone, 2-pentanone, 3-hexanone, 3-decanone, diacetyl, acetophenone, 4'-methoxy acetophenone, 4'-methyl acetophenone, propiophenone, benzophenone, 4-methoxy benzophenone, 4,4'-dimethoxy benzophenone, benzyl phenyl ketone, benzil acetone, benzoyl acetone, cyclopentanone, cyclohexanone, 4-methyl cyclohexanone, 1,2-cyclohexane dione, cycloheptanone, and acetyl acetone.

Hydroxy group-containing ketone compounds are defined as compounds having both a hydroxy group and a ketone carbonyl group in the molecule. Specific examples of preferred compounds are hydroxyacetone, acetoin, 4-hydroxy-2-butanone, 3-hydroxy-3-methyl-2-butanone, 5-hydroxy-2-butanone, diacetone alcohol, 4-(p-hydroxyphenyl)-2-butanone, 2-hydroxyacetophenone, 2'-hydroxyacetophenone, 3'-hydroxyacetophenone, 4'-hydroxyacetophenone, 4'-hydroxy-3'-methoxyacetophenone, 2-hydroxyphenyl ethyl ketone, 4'-hydroxypropiophenone, 2',4'-dihydroxyacetophenone, 2,', 5'-dihydroxyacetophenone, 2',6'-dihydroxyaceto-phenone, 3',5'-dihydroxyacetophenone, 2',3',4'-trihydroxyacetophenone, 2-hydroxybenzophenone, 4-hydroxybenzophenone, 2-hydroxy-4-methoxybenzophenone, 2-hydroxy-4-n-octyloxybenzophenone, 2,2'-dihydroxybenzophenone, 2,4-dihydroxybenzophenone, 4,4'-dihydroxybenzophenone, 2,2'-dihydroxy-4-methoxybenzo-phenone, 2,,4'-trihydroxybenzophenone, and benzoin.

As aldehyde compounds, either aliphatic or aromatic aldehyde compounds can be used. The aliphatic group in aliphatic aldehyde compounds may be either saturated or unsaturated and either linear or branched. Given as examples of preferred aldehyde compounds are formaldehyde, acetaldehyde, propionaldehyde, n-butylaldehyde, i-butylaldehyde, n-valeraldehyde, i-valeraldehyde, pivalaldehyde, n-capronaldehyde, 2-ethylhexyladehyde, n-heptaldehyde, n-caprylaldehyde, pelargonaldehyde, n-caprinaldehyde, n-undecylaldehyde, laurylaldehyde, tridecylaldehyde, myristylaldehyde, pentadecylaldehyde, palmitylaldehyde, margarylaldehyde, stearylaldehyde, glyoxal, succinaldehyde, benzaldehyde, o-tolualdehyde, m-tolualdehyde, p-tolualdehyde, α-naphthaldehyde, β-naphthaldehyde, and phenylacetnaphthaldehyde.

Examples of ester compounds are esters formed by a monobasic acid, e.g. formic acid, acetic acid, propionic acid, butyric acid, capronic acid, pelargonic acid, lauric acid, palmitic acid, stearic acid, isostearic acid, cyclohexylpropionic acid, cyclohexyl-capronic acid, benzoic acid, phenylbutyric acid, etc., a dibasic acid, e.g. oxalic acid, maleic acid, malonic acid, fumaric acid, succinic acid, glutaric acid, adipic acid, pimelic acid, suberic acid, sebacic acid, itaconic acid, phthalic acid, isophthalic acid, terephthalic acid, azelaic acid, etc., or a polybasic acid, e.g. 1,2,3-propanetricarboxylic acid, 1,3,5-n-pentanetricarboxylic acid, etc., and an alcohol, e.g., methyl alcohol, ethyl alcohol, isopropyl alcohol, n-butyl alcohol, sec-butyl alcohol, tert-butyl alcohol, amyl alcohol, hexyl alcohol, octyl alcohol, phenol, cresol, 1,3-butanediol, 1,4-butanediol, piniacol, pentaerythritol, etc.

Specific examples of lactone compounds are β-propiolactone, γ-butyrolactone, ε-caprolactone, Δα,β-crotonlactone, Δβ,γ-crotonlactone, coumarin, phthalide, α-pyrone, sydonone, fluoran, and the like.

Given as specific examples of lactam compounds are β-propiolactam, 2-pyrrolidone, 2-piperidone, ε-caprolactam, n-heptanelactam, 8-octanelactam, 9-nonanelactam, 10-decanelactam, 2-quinolone, 1-isoquinolone, oxinedole, iso-indigo, isatin, hydantoin, and quinolidinone.

Specific examples of preferred epoxy compounds include 1,3-butadiene monoxide, 1,3-butadiene dioxide, 1,2-butylene oxide, 2,3-butylene oxide, cyclohexene oxide, 1,2-epoxy cyclododecane, 1,2-epoxy decane, 1,2-epoxy eicosane, 1,2-epoxy heptane, 1,2-epoxy hexadecane, 1,2-epoxy octadecane, 1,2-epoxy octane, ethylene glycol diglycidyl ether, 1,2-epoxy heptane, 1,2-epoxy tetradecane, hexamethylene oxide, isobutylene oxide, 1,7-octadiene diepoxide, 2-phenylpropylene oxide, propylene oxide, trans-stilbene oxide, styrene oxide epoxylated 1,2-polybutadiene, epoxylated linseed oil, glycidyl methyl ether, glycidyl n-butyl ether, glycidyl allyl ether, glycidyl methacrylate, and glycidyl acrylate.

A suitable molar ratio of component (a) to component (c) when (c) is a polar ketone compound, hydroxy ketone compound, aldehyde compound, ester compound, lactone compound, lactam compound, or epoxy compound is in the range of from 10 to 1/2 and more preferably in the range of from 5 to 1 and most preferably in the range of from 2 to 1.

(c) can also be a reducing organic metal compound selected from the group consisting of aluminium compounds, zinc compounds, and magnesium compounds. Specific examples of aluminium compounds are: trimethyl aluminium, triethyl aluminium, tri-i-butyl aluminium, triphenyl aluminium, diethyl aluminium chloride, ethyl aluminium dichloride, methyl aluminium sesquichloride, ethyl aluminium sesquichloride, diethyl aluminium hydride, di-i-butyl aluminium hydride, tri(2-ethylhexyl) aluminium, aluminium tri-i-propoxide, aluminium tri-t-butoxide, and diethyl aluminium ethoxide. Examples of zinc compounds are: diethyl zinc, bis(cyclopentadienyl) zinc, and diphenyl zinc. Examples of magnesium compounds are: dimethyl magnesium, diethyl magnesium, methyl magnesium bromide, methyl magnesium chloride, ethyl magnesium bromide, ethyl magnesium chloride, phenyl magnesium bromide, phenyl magnesium chloride, and t-butyl magnesium chloride.

Beside these compounds, compounds containing two or more reducing metals, such as lithium aluminium hydride, can be used as component (c). Of the above compounds, triethyl aluminium, tri-i-butyl aluminium, diethyl aluminium chloride, ethyl aluminum dichloride, aluminium tri-i-propoxide, and aluminium tri-t-butoxide are preferred from the aspect of their ready availability and handling easiness.

When (c) is such a reducing compound, the molar ratio of component (a) and (c) is preferably greater than 1/20, more preferably from 1/1–1/18 and most preferably from 1/2–1/15.

Polymers with a high degree of hydrogenation can be obtained according to the process of the present invention, wherein the catalyst system has been surprisingly found to show a significantly higher activity in combination with a high selectivity, resulting in a higher hydrogenation rate of the starting polymer or enabling the use of a smaller concentration of catalyst per part by weight of polymer, as compared with prior art homogeneous Ti catalyst hydrogenation processes. Moreover, this catalyst can be dosed more accurately and shows an excellent reproductivity.

A clear advantage of the process of the present invention is formed by the fact that there seems not to be any distinction during hydrogenation between different types of double C—C bonds, i.e. those in 1,2 vinyl pendant groups, those in the backbone chain without substituted carbon atoms involved, and those in the backbone chain with substituted carbon atoms involved.

As the catalyst system in the present process can be applied in a significantly lower concentration, its concentration in the final hydrogenated product is much lower. The hydrogenation process can be performed at partial hydrogen pressures in the range of from 1 to 50 bar and preferably from 1 to 35 bar.

Included in the olefinically unsaturated polymers to be hydrogenated by the catalyst composition of the present invention are all polymers containing olefinically carbon— carbon unsaturated double bonds in the polymer main chain or side chains. Typical examples are conjugated diene polymers and random, block, or graft polymers of conjugated diene and olefin. Included in the above conjugated diene polymers are conjugated diene homopolymers and copolymers produced from conjugated dienes or from at least one conjugated diene and at least one olefin copolymerizable with the conjugated diene.

Typical examples of conjugated dienes used for the production of these conjugated diene polymers are conjugated dienes having 4–12 carbon atoms. Specific examples are 1,3-butadiene, isoprene, 2,3-dimethyl-1,3-butadiene, 1,3-pentadiene, 2-methyl-1,3-pentadiene, 1,3-pentadiene, 1,3-hexadiene, 4,5-diethyl-1,3-octadiene, 3-butyl-1,3-octadiene, and chloroprene.

From the aspect of manufacturing elastomers having superior characteristics and industrial advantages, 1,3-butadiene and isoprene are particularly preferred. Elastomers, such as polybutadiene, polyisoprene, butadiene/isoprene copolymers are especially preferred polymer materials used in the present invention. There are no specific limitations as to the micro-structures of the polymers. All these polymers are suitable materials in the application of the hydrogenation using the catalyst composition of the present invention.

The above-mentioned copolymers produced from at least one conjugated diene and at least one olefin copolymerizable with the conjugated diene are also suitable polymer materials to which the hydrogenation using the catalyst composition of the present invention is applied.

The above-described conjugated diene monomers can be used for the manufacture of this type of copolymers. Any olefins copolymerizable with these conjugated dienes are usable for the manufacture of the copolymer, with vinyl-substituted aromatic hydrocarbons being particular preferred. Copolymers of conjugated dienes and vinyl-substituted aromatic hydrocarbons are of particular importance for the production of industrially useful and valuable elastomers or thermoplastic elastomers. Given as specific examples of vinyl-substituted aromatic hydrocarbons used in the manufacture of this type of copolymers are styrene, $\alpha$-methylstyrene, p-methylstyrene, divinylbenzene, 1,1-diphenylethylene, N, N-dimethyl-p-aminoethylstyrene, N,N-diethyl-p-aminoethylstyrene, and vinylpyridine. Of these styrene and $\alpha$-methylstyrene are particularly preferred. Specific copolymers providing industrially valuable hydrogenated copolymers are butadiene/styrene copolymer, isoprene/styrene copolymer, and butadiene/$\alpha$-methylstyrene copolymer.

These copolymers include random copolymers in which monomers are randomly distributed throughout the polymers, progressively reducing block copolymers, complete block copolymers, and graft copolymers. The preferred copolymers are butadiene-styrene block copolymers, isoprene-styrene block copolymers, and butadiene/isoprene-styrene block copolymers of linear or radial, multiarmed shape.

In order to manufacture industrially useful thermoplastic elastomers, it is preferred that the amount of vinyl-substituted aromatic hydrocarbons is in the range of from 15 to 45% by weight. A content of vinyl bonds in the conjugated diene units of 10% or more of the total conjugated diene units is desirable for obtaining hydrogenated polymers with superior characteristics.

Included also in polymers which can be used in the hydrogenating process using the catalyst composition of the present invention are those of linear type, as well as branched type or radial or star type produced by coupling using a coupling agent. Also included in the polymers to be hydrogenated according to the present invention are those having terminals modified with polar groups after the living anionic polymerisation or by other means. Hydroxy group, carboxyl group, ester group, isocyanate group, urethane group, amide group, ureas group, and thiourethane group can be used as the polar groups. Beside the above-mentioned polymers, any polymers manufactured by any polymerisation methods, e.g., anion polymerisation, cation polymerisation, co-ordination polymerisation, radical polymerisation, solution polymerisation, emulsion polymerisation, or the like, can be used in the present invention. In addition, cyclic olefin polymers manufactured by ring-opening polymerisation using a methathesis catalyst, such as molybdenum and tungsten are included in polymers having olefinically unsaturated bonds.

In the hydrogenation reaction using the catalyst composition of the present invention, the olefinically unsaturated polymers may be hydrogenated in a condition where they are dissolved in a hydrocarbon solvent, or the olefinically unsaturated polymers may be produced by polymerisation in a hydrocarbon solvent and may be successively hydrogenated. Hydrocarbon solvents used in the hydrogenation reaction may be aliphatic hydrocarbons, e.g. pentane, hexane, heptane, octane, etc.; alicyclic hydrocarbons, e.g. cyclopentane, methyl cyclopentane, cyclohexane, etc. or aromatic solvent such as toluene. These hydrocarbon solvents may contain 20% by weight or a smaller amount of ethers such as diethyl ether, tetrahydrofuran, dibutyl ether, diethoxypropane, and dioxane.

There are no restrictions as to the concentration of polymers in carrying out the hydrogenation reaction of the present invention. Usually, however, the polymer concentration is in the range of from 1 to 30% by weight, and preferably in the range of from 3 to 20% by weight. The hydrogenation reaction is effected, after the addition of the hydrogenation catalyst composition under an inert gas atmosphere, e.g. in nitrogen or argon, or under a hydrogen atmosphere, by supplying hydrogen, with or without stirring while maintaining the temperature of the polymer solution at a specified temperature.

A temperature suitable for the hydrogenation reaction is in the range of from 0 to 150° C. A temperature lower than 0° C. is uneconomical, since at a temperature lower than 0° C. not only the catalyst activity is lowered, but also the rate of hydrogenation is retarded. If the temperature is higher than 150° C., on the other hand, not only do the polymers tend to decompose or to gel, but also aromatic rings are hydrogenated at the same time, leading to a poor hydrogenation selectivity. Preferably, the temperature is in the range of from 20 to 140° C., and more preferably in the range of from 50 to 130° C. In the hydrogenation reaction using the catalyst composition of the present invention, the reaction may be carried out at a comparatively higher temperature, resulting in a higher rate of reaction and a higher yield.

The hydrogenation reaction is carried out for a time period in the range of from 1 minute to 5 hours. The larger the amount of the catalyst composition used and the higher the pressure, the reaction time may be shorter.

It will be appreciated that another aspect of the present invention is formed by the titanium catalyst components (a) according to formula I. These catalyst components (a) are novel compounds except the unsubstituted (1-indenyl) (cyclopentadienyl) titanium dichloride and bis(1-indenyl) titanium dichloride. These compounds may be prepared by methods which are in principle known e.g. from J. Organometallic Chemistry, Issue 4, page 156–158 (1965), organometallics 1984 (3), 223, and J Am Chem. Soc. 1990, 112, 2030. More in particular the titanium compounds of formula I, wherein two indenyl groups substituted by lower alkyl or lower alkoxy or halogen or wherein one substituted indenyl and one optionally substituted cyclopentadienyl group are substituted by the hereinbefore specified groups are preferred.

The invention will now be illustrated by means of the following examples.

EXAMPLE 1

Preparation of bis(1-methylindenyl)titanium dichloride 1.36 g 1-methylindenyl lithium (10.1 mmol) were added to a solution of 0.91 g $TiCl_4$ (4.8 mmol) in 50 ml of dichloromethane at $-20°$ C. The mixture was allowed to warm to room temperature and stirred for another hour, centrifuged, and the clear solution was then decanted and evaporated in vacuo. The remainder was washed with pentane/di-ethylether and pentane to yield the desired product. 80 mg of the pure product was isolated (0.2 mmol), 2%.

EXAMPLE 2

Preparation of bis(1-(pentafluorophenyl)indenyl)-titanium dichloride 1.34 g of 1-(pentafluorophenyl)indenyl lithium (4.7 mmol) were added to solution of 0.42 g of $TiCl_4$ (2.2 mmol) in 40 ml of dichloromethane at $-20°$ C. The mixture was allowed to warm to room temperature and stirred for another hour, centrifuged, and the clear solution was then decanted and evaporated in vacuo. The remainder was washed with hexane to yield the desired product. One isomer was isolated, 265 mg (0.4 mmol), 17%.

EXAMPLE 3

Preparation of bis(5,6-dimethoxyindenyli)titanium dichloride 1.04 g of 5,6-dimethoxyindenyl lithium (4.1 mmol) were added to a solution of 0.38 g of titanium (IV) chloride (2.0 mmol) in 40 ml of dichloromethane at $-20°$ C. The mixture was allowed to warm to room temperature, stirred for another hour, and centrifuged. The clear solution was then decanted and the solvents evaporated by vacuo. The remainder was washed with diethylether (2×30 ml) and the remainder extracted with 40 ml of dichloromethane and solvent evaporated to yield 590 mg of the desired product (63%).

EXAMPLE 4

Preparation of bis(1-indenyl)dimethylsilyl titanium dichloride

η-Butyllithium (6.1 g, 1.6 M in hexane) were added to a stirred solution of dimethylsilyl-bis-indene (2 g) in dry hexane (40 ml) at $-70°$ C. The reaction mixture was allowed to warm to room temperature and was stirred for 20 hours. The white precipitate was isolated, washed with pentane, and subsequently dried under reduced pressure. The obtained powder was slowly added to a solution of $TiCl_4$ (1.5 g) in dichloromethane (60 ml) at $-70°$ C. The reaction mixture was allowed to warm to room temperature and was stirred for another hour. The formed solids were removed by centrifugation. The remaining solution was evaporated until the volatiles were removed. The crude product was washed 3 times with pentane and dried under reduced pressure. Induced crystallisation from dichloromethane with hexane yielded 60 mg (2%) rac+meso bis(1-indenyl)dimethylsilyl titanium dichloride as a very dark brown powder.

EXAMPLE 5

Preparation of bis(1-indenyl)ethylene titanium dichloride 0.96 gram $TiCl_4$ (5.07 mmol) were dissolved in 40 ml of $CH_2Cl_2$ cooled to $-40°$ C., and then 1.36 grams of bis-(1-indenyl)ethylene bis-lithium (5.07 mmol) were added as a solid. After stirring for 2 h at room temperature, the reaction mixture was centrifuged to remove LiCl. The $CH_2Cl_2$ layer was evaporated to dryness giving (1-indenyl)ethylene titanium dichloride as brown crystals which were washed twice with hexane.

EXAMPLE 6

Preparation of hydrogen terminated SBS block copolymer

A 30 liter batch of polystyrene-polybutadiene-polystyrene (SBS) block copolymer of 70,000 molecular weight was prepared by sequential anionic polymerisation using sec-butyllithium as the initiator in a stainless steel reactor. The polymerisation was conducted in cyclohexane (to which was added 140 ppm of diethoxypropane) at 18 wt % solids. The 1,2-content of the SBS polymer was 40.4 wt %.

At the end of the polymerisation reaction, the reactor was sparged with hydrogen for 2 hrs to terminate the living SBS-Li polymer and produce SBS and LiH. The LiH content of the batch was determined to be 2.2 mmol/liter.

EXAMPLE 7

Hydrogenation of SBS block copolymer with bis(indenyl) titanium dichloride

A stainless steel reactor was charged with 190 grams of SBS cement prepared as described in Example 6. The temperature of the reactor was fixed at 70° C. and the reactor was pressurised to 10 bar of hydrogen to saturate the cement. Meanwhile a suspension of 14 mg (0.04 mmol) bisindenyltitaniumdichloride in 10 ml of cylcohexane was prepared. The catalyst suspension was added to the reactor and the hydrogen pressure was raised to 50 bar. Immediately a strong exothermic reaction occurred (T=82° C.). The hydrogenation was allowed to run for 3 hours, during which period samples were drawn from the reactor and analysed by $^1H$ NMR to determine the conversion of the olefinic double bonds.

The conversion was determined to be 72 wt % after 15 min, 75 wt % after 60 min, and 77 wt % after 180 min.

EXAMPLE 8

Hydrogenation of SBS block copolymer with bis(indenyl) titanium dichloride

A stainless steel reactor was charged with 800 grams of SBS cement prepared as described in Example 6. The temperature of the reactor was fixed at 50° C. and the reactor was pressurised to 10 bar of hydrogen to saturate the cement. Meanwhile, a suspension of 29 mg (0.084 mmol) bisindenyltitaniumdichloride in 10 ml of cyclohexane was prepared. The catalyst suspension was added to the reactor and the hydrogen pressure was raised to 50 bar. Immediately an exothermic reaction occurred. The hydrogenation was allowed to run for 3 hours, during which period samples were drawn from the reactor and analysed by $^1H$ NMR to determine the conversion of the olefinic double bonds. Following the same procedure two more runs with 58 mg (0.168 mmol) and 87 mg (0.252 mmol) of bisindenyltitaniumdichloride were carried out. The results are summarised in Table 1.

TABLE 1

Hydrogenation results with different amounts of bisindenyltitanium dichloride

| Amount (mmol) | 15 min. conv. (wt %) | 60 min conv. (wt %) | 180 min conv. (wt %) |
|---|---|---|---|
| 0.084 | 15 | 46 | 88 |
| 0.168 | 22 | 88 | 90 |
| 0.252 | 27 | 89 | 91 |

COMPARATIVE EXAMPLE
Hydrogenation of SBS block copolymer with bis(cyclopentadienyl)titanium dichloride A stainless steel reactor was charged with 800 grams of SBS cement prepared as described in Example 6. The temperature of the reactor was fixed at 50° C. and the reactor was pressurised to 10 bar of hydrogen to saturate the cement. Meanwhile a suspension of 21 mg (0.084 mmol) biscyclopentadienyltitaniumdichloride in 10 ml of cyclohexane was prepared. The catalyst suspension was added to the reactor and the hydrogen pressure was raised to 50 bar. The hydrogenation was allowed to run for 3 hours, during which period samples were drawn from the reactor and analysed by 1H NMR to determine the conversion of the olefinic double bonds. The conversion was determined to be 22 wt % after 15 min, 51 wt % after 60 min, and 60 wt % after 180 min, which is considerably lower than with the same amount of bisindenyltitanium dichloride as shown in Examples 7 and 8.

EXAMPLE 9–11
Hydrogenation of SBS block copolymer with substituted bis(indenyl)titanium dichloride compounds Following the same procedure as described in example 7, three more hydrogenation experiments were carried out using 0.04 mmol of the catalysts prepared in examples 1–3. The results are shown in Table 2.

TABLE 2

Hydrogenation results with different indenyltitanium catalysts

| Catalyst from: | 15 min conv. (wt %) | 60 min conv. (wt %) | 180 min conv. (wt %) |
|---|---|---|---|
| Example 1 | 47 | 79 | 81 |
| Example 2 | 7 | 12 | 20 |
| Example 3 | 27 | 91 | 96 |

EXAMPLE 12–14
Hydrogenation of SBS block copolymer with bis(indenyl) titanium dichloride in the presence of dimethyloxalate A stainless steel reactor was charged with 190 grams of SBS cement prepared as described in Example 6. To the reactor was added 4.7 mg (0.04 mmol) dimethxyloxalate in 10 ml of cyclohexane. The temperature of the reactor was fixed at 70° C. and the reactor pressurised to 10 bar of hydrogen to saturate the cement. Meanwhile a suspension of 14 mg (0.04 mmol) bisindenyltitanium-dichloride in 10 ml of cyclohexane was prepared. The catalyst suspension was added to the reactor and the hydrogen pressure was raised to 50 bar. The hydrogenation was allowed to run for 3 hours, during which period samples were drawn from the reactor and analysed by $^1$H NMR to determine the conversion of the olefinic double bonds. The results are shown in Table 3.

TABLE 3

Hydrogenation results with bisindenyltitanium dichloride modified with dimethyloxalate

| modifier/Ti | 15 min conv. (wt %) | 60 min conv. (wt %) | 180 min conv. (wt %) |
|---|---|---|---|
| 1:1 | 20 | 55 | 83 |
| 0.5:1 | 76 | 83 | 88 |
| 0.75:1 | 77 | 80 | 87 |

EXAMPLES 15–16
Hydrogenation of SBS block copolymer with bridged bis(indenyl)titanium dichloride compounds Following the same procedure as described in example 7, two more hydrogenation experiments were carried out using 0.04 mmol of the catalysts of examples 4 and 5. The results are shown in Table 4.

TABLE 4

Hydrogenation results with bridged bisindenyltitanium compounds

| Catalyst | 15 min conv. (wt %) | 60 min conv. (wt %) | 180 min conv. (wt %) |
|---|---|---|---|
| Example 4 | 29 | 33 | 36 |
| Example 5 | 32 | 47 | 48 |

It will be appreciated from Examples 15 and 16 as compared to examples 7–12, that introduction of a bridging substituent between the indenyl groups certainly does not improve the hydrogenation process.

EXAMPLE 17
Hydrogenation of SBS block copolymer with (indenyl)(cyclopentadienyl)titanium dichloride A stainless steel reactor was charged with 800 grams of SBS cement prepared as described in Example 6. The temperature of the reactor was fixed at 50° C. and the reactor was pressurised to 10 bar of hydrogen to saturate the cement. Meanwhile a suspension of 0.109 mmol of (indenyl)(cyclopentadienyl)titanium dichloride in 10 ml of cyclohexane was prepared. The catalyst suspension was added to the reactor and the hydrogen pressure was raised to 50 bar. Immediately an exothermic reaction occurred. The hydrogenation was allowed to run for 3 hours, during which period samples were drawn from the reactor and analysed by $^1$ NMR to determine the conversion of the olefinic double bonds. Following the same procedure, two more runs with 0.109 mmol of (5-methoxyindenyl) (cyclopentadienyl) titanium dichloride and (5,6-dimethoxyindenyl) (cyclopentadienyl) titanium dichloride were carried out. The results are summarised in Table 5.

TABLE 5

Hydrogenation results with optionally substitued (indenyl) (cyclopentadienyl) titanium dichlorides

| Catalyst | 15 min conv. (wt %) | 60 min conv. (wt %) | 180 min conv. (wt %) |
|---|---|---|---|
| IndCpTiCl$_2$ | 17 | 70 | 98 |
| MeOIndCpTiCl$_2$ | 13 | 37 | 96 |
| (MeO)$_2$IndCpTiCl$_2$ | 13 | 37 | 99 |

We claim:

1. A process for the selective hydrogenation of poly(vinyl aromatic hydrocarbon)/poly(conjugated diene) polymers containing ethylenical unsaturation comprising bringing a solution of such polymers in intensive contact with hydrogen in the presence of a catalyst composition which comprises:

(a) a titanium compound of the formula

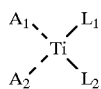

(I) wherein $A_1$ represents an optionally substituted indenyl group of the formula

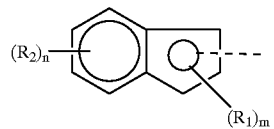

wherein substituents $R_1$ and $R_2$ may be the same or different and each may be selected from halogen, phenyl which optionally may bear one or more the same or different substituents, lower alkyl, alkoxy, phenoxy, phenylalkoxy, benzyl, and a bulky substituent containing one or more hetero atoms such as tri (loweralkyl)silyl, —NPh$_2$, —NHPh, —BPh$_2$ and —B(OPh)$_2$, wherein n may be an integer of from 0 to 4, and m may be an integer of from 0 to 3;

(II) wherein $A_2$ has the same meaning as $A_1$ or alternatively represents an optionally substituted cyclopentadienyl group, and wherein $L_1$ and $L_2$ may be the same or different and each may be selected from hydrogen, halogen, lower alkyl, phenyl, aralkyl having from 7 to 10 carbons, a lower alkoxy group, phenyloxy, phenylalkoxy group having from 7 to 10 carbon atoms, carboxyl, carbonyl, a B-diketone coordination, a —CH$_2$P(Phenyl)$_2$, —CH$_2$ Si(lower alkyl)$_3$, or —P(phenyl)$_2$ group; and (b) an alkali metal hydride, added as such or prepared in situ in the polymer solution from the alkali metal terminated living polymer and/or from additionally added alkali metal alkyl.

2. The process of claim 1 characterized in that the molar ratio alkali metal:titanium is at least 2:1.

3. The process of claim 1 characterized in that the alkalimetal hydride is lithium hydride.

4. The process of claim 3 characterized in that the molar ratio of lithium hydride to titanium is in the range of from 6 to 25.

5. The process of claim 1 characterized in that ligands $L_1$ and $L_2$ in component (a) are selected from chlorine, bromine, carbonyl, methyl, ethyl, n-propyl, isopropyl, n-butyl, tert-butyl, sec-butyl, trimethylsilyloxy, benzyl, phenyl, hexyl, methoxy, ethoxy, n-propoxy, isopropoxy, butoxy, tert-butoxy, sec-butoxy, pentoxy, neopentoxy, phenoxy, phenylmethoxy, phenylethoxy, and a CH$_2$P (phenyl)$_2$ group.

6. The process of claim 5 characterised in that $L_1$ and $_2$ are both chlorine, benzyl, phenyl, methoxy, ethoxy, isopropoxy, tert-butoxy, n-butoxy, phenoxy, or a CH$_2$P(phenyl)$_2$ group.

7. The process of claim 6 characterised in that $L_1$ and $_2$ are both chlorine.

8. The process of claim 1 characterised in that the component (a) is selected from the group consisting of bis(1-indenyl) titanium dichloride, bis(1-indenyl) titanium diphenoxide, bis(1-indenyl) titanium dimethoxide, bis(1-methylindenyl) titanium dichloride, bis(5,6-dimethoxy-indenyl) titanium dichloride, bis(dimethoxyindenyl) titanium dichloride, bis(trimethyl-silylindenyl) titanium dichloride, (dimethoxyindenyl) (cyclopenta-dienyl) titanium dichloride, (dimethoxyindenyl) (indenyl) titanium dichloride, (dimethoxyindenyl) (indenyl) titanium dimethoxide, (methoxyindenyl) (indenyl) titanium dichloride, (methoxyindenyl) (indenyl) titanium dimethoxide, (1-indenyl) (cyclopentadienyl) titanium dichloride, (1-indenyl) (cyclopentadienyl) titanium dimethoxide, and (1-indenyl) (cyclopentadienyl) titanium diphenoxide.

9. The process of claim 1 characterised in that it also comprises one or more promoters (c) which are selected from the group consisting of polar ketone compounds, hydroxy group-containing ketone compounds, aldehyde compounds, ester compounds, lactone compounds, lactam compounds, and epoxy compounds.

10. The process of claim 9 characterised in that it comprises a promoter selected from the group consisting of ketone compounds, hydroxy group-containing ketone compounds, aldehyde compounds, ester compounds, and epoxy compounds.

11. The process of claim 9 characterised in that the molar ratio of component (a) to component (c) is in the range of from 10 to 1/2.

12. The process of claim 11 characterised in that the molar ratio is in the range of from 2 to 1.

13. The process of claim 1 characterised in that it also comprises one or more promoters (c) which are reducing organic metal compounds selected from the group consisting of aluminium compounds, zinc compounds, and magnesium compounds.

14. The process of claim 13 characterised in that the molar ratio of component (a) and (c) is in the range of from 1/1 to 1/18.

15. The process of claim 14 characterised in that the molar ratio of component (a) and (c) is in the range of from 1/2 to 1/15.

* * * * *